(12) United States Patent
Ecker et al.

(10) Patent No.: US 6,355,778 B1
(45) Date of Patent: Mar. 12, 2002

(54) PLANT GENES FOR SENSITIVITY TO ETHYLENE AND PATHOGENS

(75) Inventors: Joseph Ecker, Erial, NJ (US); Jose Alonso, Philadelphia, PA (US)

(73) Assignee: The Trustees of the University of Pennsylvania, PA (US)

( * ) Notice: Subject to any disclaimer, the term of this patent is extended or adjusted under 35 U.S.C. 154(b) by 0 days.

(21) Appl. No.: 09/400,348

(22) Filed: Sep. 20, 1999

Related U.S. Application Data

(60) Division of application No. 08/819,288, filed on Mar. 18, 1997, now Pat. No. 5,955,652, which is a continuation-in-part of application No. 08/261,822, filed on Jun. 17, 1994, now Pat. No. 5,650,553, which is a continuation-in-part of application No. 08/003,311, filed on Jan. 12, 1993, now Pat. No. 5,444,166, which is a continuation-in-part of application No. 07/928,464, filed on Aug. 10, 1992, now Pat. No. 5,367,065, application No. 09/400,348, which is a continuation-in-part of application No. 07/899,262, filed on Jun. 16, 1992, now abandoned.

(51) Int. Cl.$^7$ .............................. A01H 4/00; A01H 3/00; A01H 5/00; C12N 1/06; A01N 25/00
(52) U.S. Cl. ........................ 530/370; 435/410; 435/419; 435/430; 435/468; 800/283; 800/289
(58) Field of Search .................................. 800/283, 289; 435/69.8, 320.1, 468, 410, 419, 430; 530/370; 536/23.6

*Primary Examiner*—James Housel
*Assistant Examiner*—Bao Qun Li
(74) *Attorney, Agent, or Firm*—Evelyn H. McConathy; Dilworth Paxson LLP

(57) ABSTRACT

The present invention is directed to amino acid sequences for ethylene insensitive, EIN loci in the ethylene response in plant systems.

1 Claim, 2 Drawing Sheets

PLANT GENES FOR SENSITIVITY TO ETHYLENE AND PATHOGENS

This application is a divisional application of U.S. application Ser. No. 08/819,288, filed Mar. 18, 1997, now U.S. Pat. No. 5,955,652, which is a continuation-in-part of U.S. application Ser. No. 08/261,822, filed Jun. 17, 1994, now U.S. Pat. No. 5,650,553, which is a continuation-in-part of U.S. application Ser. No. 08/003,311, filed Jan. 12, 1993, now U.S. Pat. No. 5,444,166, which is a continuation-in-part of U.S. application Ser. No. 07/928,464, filed Aug. 10, 1992, now U.S. Pat. No. 5,367,065, this application is also a continuation-in-part of U.S. application Ser. No. 07/899,262, filed Jun. 16, 1992, now abandoned; the disclosures of each of which are hereby incorporated in their entirety.

REFERENCE TO GOVERNMENT GRANTS

This work was supported in part by research grants from the National Institutes of Health GM-26379 and National Science Foundation grant IBN-92-05342. The United States Government may have certain rights in this invention.

BACKGROUND OF THE INVENTION

Ethylene, a gaseous plant hormone, is involved in the regulation of a number of plant processes ranging from growth and development to fruit ripening. As in animal systems, response of plants to disease not only involves static processes, but also involves inducible defense mechanisms. One of the earliest detectable event to occur during plant-pathogen interaction is a rapid increase in ethylene biosynthesis. Ethylene biosynthesis, in response to pathogen invasion, correlates with increased defense mechanisms, chlorosis, senescence and abscission. The molecular mechanisms underlying operation of ethylene action, however, are unknown. Nonetheless, ethylene produced in response to biological stress is known to regulate the rate of transcription of specific plant genes. A variety of biological stresses can induce ethylene production in plants including wounding, bacterial, viral or fungal infection as can treatment with elicitors, such as glycopeptide elicitor preparations (prepared by chemical extraction from fungal pathogen cells). Researchers have found, for example, that treatment of plants with ethylene generally increases the level of many pathogen-inducible "defense proteins", including β-1,3-glucanase, chitinase, L-phenylalanine ammonia lyase, and hydroxyproline-rich glycoproteins. The genes for these proteins can be transcriptionally activated by ethylene and their expression can be blocked by inhibitors of ethylene biosynthesis. Researchers have also characterized a normal plant response to the production or administration of ethylene, as a so-called "triple response". The triple response involves inhibition of root and stem elongation, radial swelling of the stem and absence of normal geotropic response (diageotropism).

Ethylene is one of five well-established plant hormones. It mediates a diverse array of plant responses including fruit ripening, leaf abscission and flower senescence.

The pathway for ethylene biosynthesis has been established. Methionine is converted to ethylene with S-adenylmethionine (SAM) and 1-aminocyclopropane-1-carboxylic acid (ACC) as intermediates. The production of ACC from SAM is catalyzed by the enzyme ACC synthase. Physiological analysis has suggested that this is the key regulatory step in the pathway, see Kende, *Plant Physiol.* 1989, 91, 1–4. This enzyme has been cloned from several sources, see Sato et al., *PNAS,* (USA) 1989, 86, 6621; Van Der Straeten et al., *PNAS,* (USA) 1990, 87, 4859–4863; Nakajima et al., *Plant Cell Physiol.* 1990, 29, 989. The conversion of ACC to ethylene is catalyzed by ethylene forming enzyme (EFE), which has been recently cloned (Spanu et al., *EMBO J* 1991, 10, 2007. Aminoethoxyvinylglycine (AVG) and α-aminoisobutyric acid (AIB) have been shown to inhibit ACC synthase and EFE respectively. Ethylene binding is inhibited non-competitively by silver, and competitively by several compounds, the most effective of which is trans-cyclooctane. ACC synthase is encoded by a highly divergent gene family in tomato and Arabidopsis (Theologis, A., *Cell* 70:181 (1992)). ACC oxidase, which converts ACC to ethylene, is expressed constitutively in most tissues (Yang et al., *Ann. Rev. Plant Physiol* 1984, 35, 155), but is induced during fruit ripening (Gray et al. *Cell* 1993 72, 427). It has been shown to be a dioxygenase belonging to the $Fe^{2+}$/ascorbate oxidase superfamily (McGarvey et al., *Plant Physiol* 1992, 98, 554).

Etiolated dicotyledonous seedlings are normally highly elongated and display an apical arch-shaped structure at the terminal part of the shoot axis; the apical hook. The effect of ethylene on dark grown seedlings, the triple response, was first described in peas by Neljubow in 1901, Neljubow, D., *Pflanzen Beih. Bot. Zentralb.,* 1901, 10, 128. In Arabidopsis, a typical triple response consists of a shortening and radial swelling of the hypocotyl, an inhibition of root elongation and an exaggeration of the curvature of the apical. Etiolated morphology is dramatically altered by stress conditions which induce ethylene production the ethylene-induced "triple response" may provide the seedling with additional strength required for penetration of compact soils, see Harpham et al., *Annals of Bot.,* 1991, 68, 55. Ethylene may also be important for other stress responses. ACC synthase gene expression and ethylene production is induced by many types of biological and physical stress, such as wounding and pathogen infection, see Boller, T., in *The Plant Hormone Ethylene,* A. K. Mattoo and J. C. Suttle eds., 293–314, 1991, CRC Press, Inc. Boca Raton and Yu, Y. et al., *Plant Phys.,* 1979, 63,589, Abeles et al. 1992 Second Edition San Diego, Calif. Academic Press; and Gray et al. *Plant Mol Biol.* 1992 19, 69.

A number of researchers have identified the interaction between *Arabidopsis thaliana* and *Pseudomonas syringae* bacteria; Whalen et al., "Identification of *Pseudomonas syringae* Pathogens of Arabidopsis and a Bacterial Locus Determining Avirulence on Both Arabidopsis and Soybean", *The Plant Cell* 1991, 3, 49, Dong et al., "Induction of Arabidopsis Defense Genes by Virulent and Avirulent *Pseudomonas syringae* Strains and by a Cloned Avirulence Gene", *The Plant Cell* 1991, 3, 61, and Debener et al., "Identification and Molecular Mapping of a Single *Arabidopsis thaliana* Locus Determining Resistance to a Phytopathogenic *Pseudomonas syringae* Isolate", *The Plant Journal* 1991, 1, 289. *P. syringae* pv. *tomato* (Pst) strains are pathogenic on Arabidopsis. A single bacterial gene, avrRpt2, was isolated that controls pathogen avirulence on specific Arabidopsis host genotype Col-0.

Bent, A. F., et al., "Disease Development in Ethylene-Insensitive *Arabidopsis thaliana* Infected with Virulent and Avirulent Pseudomonas and Xanthomonas Pathogens", *Molecular Plant-Microbe Interactions* 1992, 5, 372; Agrios, G. N., *Plant Pathology* 1988, 126, Academic Press, San Diego; and Mussel, H., "Tolerance to Disease", page 40, in *Plant Disease: An Advanced Treatise,* Volume 5, Horsfall, J. G. and Cowling, E. B., eds., 1980, Academic Press, New York, establish the art recognized definitions of tolerance, susceptibility, and resistance. Tolerance is defined for purposes of the present invention as growth of a pathogen in a plant where the plant does not sustain damage. Resistance is defined as the inability of a pathogen to grow in a plant and no damage to the plant results. Susceptibility is indicated by pathogen growth with plant damage.

Regardless of the molecular mechanisms involved, the normal ethylene response of a plant to pathogen invasion has been thought to have a cause and effect relationship in the ability of a plant to fight off plant pathogens. Plants insensitive in any fashion to ethylene were believed to be incapable of eliciting a proper defense response to pathogen invasion, and thus unable to initiate proper defense mechanisms. As such, ethylene insensitive plants were thought to be less disease tolerant.

The induction of disease responses in plants requires recognition of pathogens or pathogen-induced symptoms. In a large number of plant-pathogen interactions, successful resistance is observed when the plant has a resistance gene with functional specificity for pathogens that carry a particular avirulence gene. If the plant and pathogen carry resistance and avirulence genes with matched specificity, disease spread is curtailed and a hypersensitive response involving localized cell death and physical isolation of the pathogen typically occurs. In the absence of matched resistance and avirulence genes, colonization and tissue damage proceed past the site of initial infection and disease is observed.

A better understanding of plant pathogen tolerance is needed. Also needed is the development of methods for improving the tolerance of plants to pathogens, as well as the development of easy and efficient methods for identifying pathogen tolerant plants.

Genetic and molecular characterization of several gene loci and protein products is set forth in the present invention. The results will reveal interactions among modulatory components of the ethylene action pathway and provide insight into how plant hormones function. Thus, the quantity, quality and longevity of food, such as fruits and vegetables, and other plant products such as flowers, will be improved thereby providing more products for market in both developed and underdeveloped countries.

SUMMARY OF THE INVENTION

The present invention is directed to nucleic acid sequences for ethylene insensitive, EIN loci and corresponding amino acid sequences. Several ein wild type sequences, mutations, amino acid sequences, and protein products are included within the scope of the present invention. The nucleic acid sequences from *Arabidopsis thaliana* Columbia-0 strain set forth in SEQ ID NOS 1 and 2 for ein2 genomic DNA and cDNA, respectively, as well as the EIN2 amino acid sequence set forth in SEQ ID NO: 3 are particular embodiments of the present invention.

These and other aspects of the invention will become more apparent from the following detailed description.

BRIEF DESCRIPTION OF THE FIGURES

FIG. 2A displays Col-O wild-type plants, FIG. 2B displays transgenic pKYLX7:cEIN2-containing Col-O plants.

DETAILED DESCRIPTION OF THE INVENTION

Figure 1:
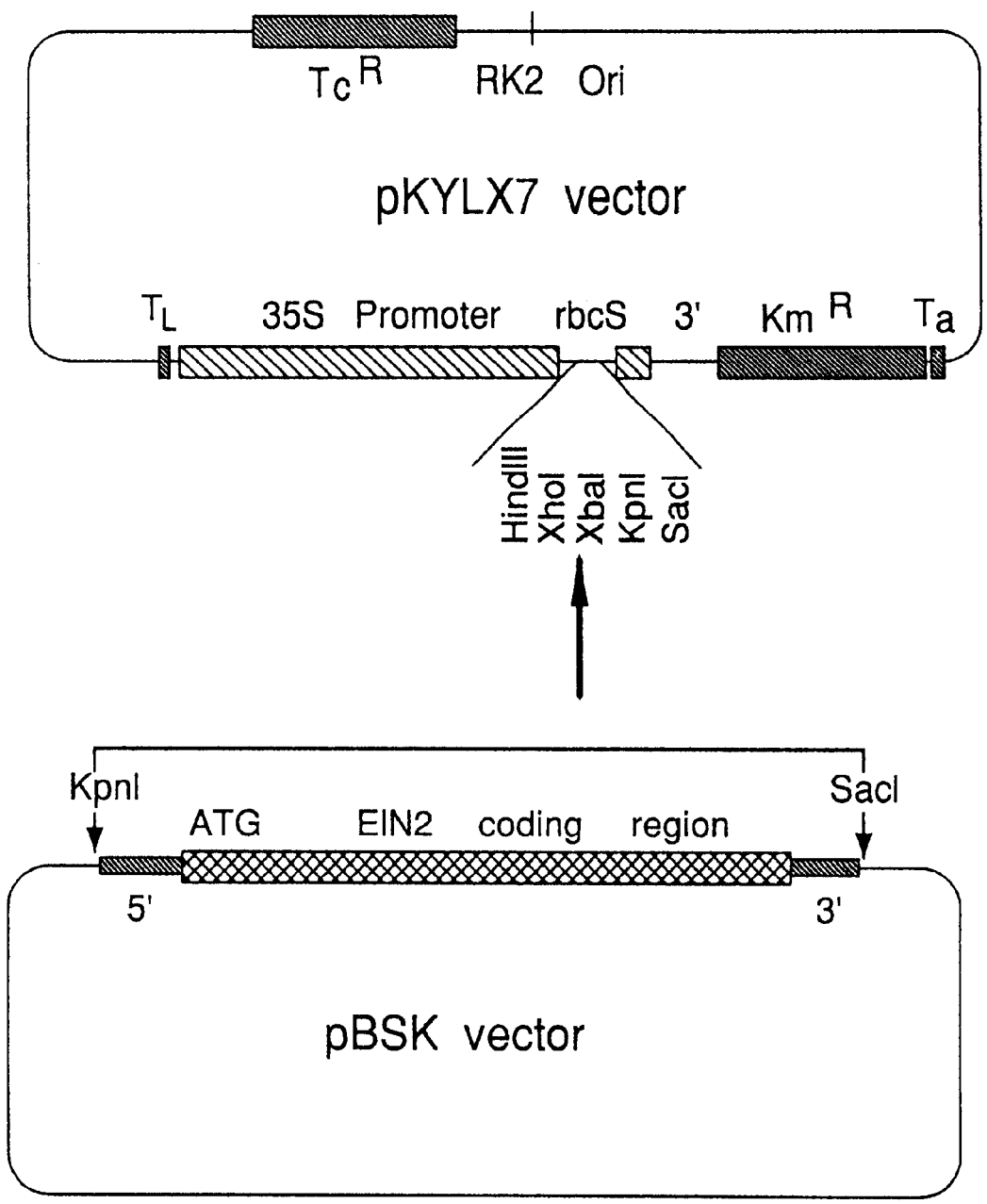
FIG. 1 sets forth the construction of pKYLX7:cEIN2 vector from pBSK:cEIN2 vector.

The present invention is directed to nucleic acid and amino acid sequences which lend valuable characteristics to plants.

The present invention is directed to nucleic acid sequences of the EIN2 locus of *Arabidopsis thaliana* Columbia-0 strain. Wild type and mutant sequences of EIN2 are within the scope of the present invention. Amino acid and protein sequences corresponding to the nucleic acid sequences are included in the present invention. EIN2 mutations provide for ethylene insensitivity and pathogen tolerance in plants.

SEQ ID NO: 2, that provides for an isolated cDNA representing the nucleic acid sequence coding for EIN2, and SEQ ID NO: 1 that provides for an isolated genomic EIN2 sequence, are embodiments of the present invention. The purified amino acid sequence of SEQ ID NO: 3 represents the EIN2 amino acid sequence or protein product encoded by the cDNA identified above. A cDNA sequence represented by bases 584–4468 of SEQ ID NO: 2 encodes an amino acid sequence set forth in SEQ ID NO: 3, represented therein as amino acids 1-1295. EIN2 mutations identified herein by nucleotide position are measured in accordance with the beginning of the cDNA.

In accordance with the present invention, nucleic acid sequences include and are not limited to DNA, including and not limited to cDNA and genomic DNA; RNA, including and not limited to mRNA and tRNA; and suitable nucleic acid sequences such as those set forth in SEQ ID NOS set forth herein, and alterations in the nucleic acid sequences including alterations, deletions, mutations and homologs. In addition, mismatches within the sequences identified above, which achieve the methods of the invention, are also considered within the scope of the disclosure. The sequences may also be unmodified or modified. Any change in the sequences that permits substantially the same sequence to be useful in substantially the same way is within the scope of the present invention. In addition, the isolated, or purified, sequences of the present invention may be natural, recombinant, synthetic, or a combination thereof. Activity associated with the sequences of the present invention include, inter alia, all or part of a sequence of the present invention, or a sequence substantially similar thereto.

Also amino acid, peptide and protein sequences within the scope of the present invention include, and are not limited to, the sequences set forth herein and alterations in the amino acid sequences including alterations, deletions, mutations and homologs.

In accordance with the invention, the nucleic acid sequences employed in the invention may be exogenous/heterologous sequences. Exogenous and heterologous, as used herein, denote a nucleic acid sequence which is not obtained from and would not normally form a part of the genetic make-up of the plant or the cell to be transformed, in its untransformed state. Plants comprising exogenous nucleic acid sequences of EIN2 and ein2 mutations, such as and not limited to the nucleic acid sequences of SEQ ID NOS set forth herein are within the scope of the invention.

Transfected and/or transformed plant cells comprising nucleic acid sequences of EIN2 and ein2 mutations, such as and not limited to the nucleic acid sequences of SEQ ID NOS set forth herein, are within the scope of the invention. Transfected cells of the invention may be prepared by employing standard transfection techniques and procedures as set forth in Sambrook et al., *Molecular Cloning: A Laboratory Manual*, 2nd ed., 1989, Cold Spring Harbor Laboratory Press, Cold Spring Harbor, N.Y., hereby incorporated by reference in its entirety.

In accordance with the present invention, mutant plants which may be created with the sequences of the claimed invention include higher and lower plants in the Plant Kingdom. Mature plants and seedlings are included in the scope of the invention. A mature plant includes a plant at any stage in development beyond the seedling. A seedling is a very young, immature plant in the early stages of development.

Particularly preferred plants are those from: the Family Umbelliferae, particularly of the genera Daucus (particularly the species *carota,* carrot) and Apium (particularly the species *graveolens dulce,* celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *sativa* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana.* ein2 mutant sequences render plants disease and pathogen tolerant, and ethylene insensitive. For purposes of the current invention, disease tolerance is the ability of a plant to survive infection with minimal injury or reduction in the harvested yield of saleable material. Plants with disease tolerance may have extensive levels of infection but have little necrosis and few to no lesions. These plants may also have reduced necrotic and water soaking responses and chlorophyll loss may be virtually absent. In contrast, resistant plants generally limit the growth of pathogens and contain the infection to a localized area with multiple apparent injurious lesions.

The current invention is directed to, for example, identifying plant tolerance to bacterial infections including, but not limited to *Clavibacter michiganense* (formerly *Coynebacterium michiganense*), *Pseudomonas solanacearum* and *Erwinia stewartii,* and more particularly, *Xanthomonas campestris* (specifically pathovars *campestris* and *vesicatoria*), *Pseudomonas syringae* (specifically pathovars *tomato, maculicola*).

In addition to bacterial infections, disease tolerance to infection by other plant pathogens is within the scope of the invention. Examples of viral and fungal pathogens include, but are not limited to tobacco mosaic virus, cauliflower mosaic virus, turnip crinkle virus, turnip yellow mosaic virus; fungi including *Phytophthora infestans, Peronospora parasitica, Rhizoctonia solani, Botrytis cinerea, Phoma lingam* (*Leptosphaeria maculans*), and *Albugo candida.*

Like ein2, ein3 mutants also exhibit ethylene insensitivity. However, ein3 mutants do not exhibit disease or pathogen tolerance. Ethylene, $CH_2=CH_2$, is a naturally occurring plant hormone. The ethylene regulatory pathway includes the ethylene biosynthesis pathway and the ethylene autoregulatory or feedback pathway. In the ethylene biosynthesis pathway, methionine is converted to ethylene with S-adenosylmethionine (SAM) and 1-aminocyclopropane-1-carboxylic acid (ACC) as intermediates. These two reactions are catalyzed by ACC synthase and ethylene-forming enzyme (EFE), respectively. Little is known about the enzymes catalyzing these reactions and their regulation at the molecular level.

The receptor and receptor complex are believed to function with the autoregulatory pathway in the control of ethylene production. Inhibitors of the pathway include AVG (aminoethoxyvinyl-glycine) and AIB (α-aminoisobutyric acid).

In accordance with the claimed invention, ethylene insensitive plants are those which are unable to display a typical ethylene response when treated with high concentrations of ethylene. For purposes of the present invention, ethylene insensitivity includes total or partial inability to display a typical ethylene response. A typical ethylene response in wild type plants includes, for example, the so-called "triple response" which involves inhibition of root and stem elongation, radial swelling of the stem, and absence of normal geotropic response (diageotropism). Thus, for example, ethylene insensitive plants may be created in accordance with the present invention by the presence of an altered "triple response" wherein the root and stem are elongated despite the presence of high concentrations of ethylene. Further, a typical ethylene response also includes a shut down or diminution of endogenous ethylene production, upon application of high concentrations of ethylene. Ethylene insensitive plants may thus also be screened for, in accordance with the present invention, by the ability to continue production of ethylene, despite administration of high concentrations of ethylene. Such ethylene insensitive plants are believed to have impaired receptor function such that ethylene is constitutively produced despite the presence of an abundance of exogenous ethylene.

Screening includes screening for root or stem elongation and screening for increased ethylene production. Ethylene sensitive wild type plants experience an inhibition of root and stem elongation when an inhibitory amount of ethylene is administered. By inhibition of root and stem elongation, it is meant that the roots and stems grow less than the normal state (that is, growth without application of an inhibitory amount of ethylene). Typically, normal Arabidopsis (Col) grown without ethylene or ethylene precursor aminocyclopropane, ACC, root elongation is about 6.5±0.2 mm/3 days; normal stem elongation is 8.7±0.3 mm/3 days. In the presence of 100 $\mu$m ACC, Col root growth is 1.5±0.04 mm/3 days and stem growth of 3.2±0.1 mm/3 days for Col. Alternatively, plants may be sprayed with ethaphon or ethrel. By roots, as used here, it is meant mature roots (that is, roots of any plant beyond the rudimentary root of the seedling), as well as roots and root radicles of seedlings. Stems include hypocotyls of immature plants of seedlings and stems, and plant axes of mature plants (that is, any stem beyond the hypocotyl of seedlings).

Ethylene sensitive wild type plants experience a shut down or diminution of endogenous ethylene production, upon application of high concentrations of ethylene. In the ethylene insensitive plants of the present invention, the plants continue endogenous production of ethylene, despite administration of inhibitory amounts of ethylene. An ethylene insensitive plant will produce an amount or have a rate of ethylene production greater than that of a wild type plant upon administration of an inhibitory amount of ethylene. As one skilled in the art will recognize, absolute levels of ethylene produced will change with growth conditions.

Ein1 and ein2 mutants are described for example in, Guzman et al., "Exploiting the Triple Response of Arabidopsis to Identify Ethylene-Related Mutants", *The Plant Cell* 1990, 2, 513, the disclosures of which are hereby incorporated herein by reference, in their entirety.

The present invention is further described in the following example. The example is not to be construed as limiting the scope of the appended claims.

EXAMPLE 1
Cloning and Sequencing of EIN2

Genomic DNA was isolated from several leaves (2–3) of adult Arabidopsis plants (ecotype Columbia) using a C-TAB DNA miniprep procedure set forth in Doyle, J. J., Doyle, J. L. 1987 Phytochem Buee 19:11–15, incorporated herein by reference in its entirety.

Using specific primers, different fragments of the EIN2 gene covering the complete gene were amplified, see Table 1. The following conditions were used for the PCR amplification: each reaction of 50 μl contained: 50 ng genomic DNA, 20 pmol of each primer, 5 units of taq DNA polymerase, 25 mM $MgCl_2$ and dATP, dCTP, dGTP, dTTP 20 μM each. For the PCR, and ERICOMP PCR thernocycler Twinblok system (Ericomp, Inc., San Diego, Calif.) was used. The PCR conditions were 94° C. for 30 seconds, 54–58° C. (depending on the melting temperature of the primer) 30 seconds, and 72° C. for 1–3 minutes (depending on the expected length of the product).

PCR products were purified from agarose gels using Genclean kitII in accordance with the manufacturer's instructions (Genclean kitII, Bio101, Inc., Vista, Calif.). About 400 ng of the purified DNA was sequenced in an Applied Biosystem automated DNA sequencer (model 373A) (Applied Biosystem Div., Perkin Elmer Corporation, Foster City, Calif.)using dye terminators as recommended by the manufacturer. Each fragment was sequenced several times (4–8) using different genomic DNA minipreps.

TABLE 1

| PCR PRIMERS | EIN2 FRAGMENT AMPLIFIED | SEQUENCING PRIMERS | EIN2 FRAGMENT SEQUENCED |
| --- | --- | --- | --- |
| PE24 & PE22 | 268 TO 1718 | PE27 | 638 TO 878 |
| PE25 & PE22 | 916 TO 1718 | PE25 | 958 TO 1428 |
| | | PE22 | 1384 TO 1656 |
| PE26 & PE6 | 1160 TO 2528 | PE1 | 1758 TO 2278 |
| PE8 & PE2.7B | 1928 TO 2848 | PE8 | 2058 TO 2358 |
| | | PE6 | 2068 TO 2498 |
| | | PE14 | 2288 TO 2678 |
| | | PE2.7B | 2568 TO 2798 |
| PE2.7A & PE12 | 2698 TO 368 | PE2.7A | 2768 TO 3188 |
| | | PE11 | 3018 TO 3228 |
| PE5 & PE16 | 3168 TO 3888 | PE12 | 3208 TO 3608 |
| | | PE5 | 3508 TO 3888 |
| PE20 & PE2 | 3938 TO 5568 | PE20 | 3898 TO 4298 |
| | | PE4 | 4128 TO 4478 |
| | | PE13 | 4497 TO 4739 |
| PE2 & PE4 | 4068 TO 5628 | PE9 | 4811 TO 5144 |
| | | PE10A | 5060 TO 5428 |
| PE10A & PE2.5 | 5018 TO 6004 | PE17 | 5478 TO 5753 |
| | | PE2.5 | 5633 TO 5933 |

TABLE 2

PRIMERS AND SEQ ID NOS

| SEQUENCE ID NO. | Primer Name | Sequence |
| --- | --- | --- |
| 4 | PE2.7A | GGATCCTCTAGTCAAATTACCGC |
| 5 | PE2.7B | AGATCTGGTATATTCCGTCTGCAC |
| 6 | PE2.5 | CCGGATTCGGTTTGTAGC |

TABLE 2-continued

PRIMERS AND SEQ ID NOS

| SEQUENCE ID NO. | Primer Name | Sequence |
| --- | --- | --- |
| 7 | PE2 | GAAAGCCACATCACCTGC |
| 8 | PE4 | GACACCGGGAAGTATCG |
| 9 | PE5 | CTGCTTTCATAGAAGAGGC |
| 10 | PE6 | GTCAGAACAAACCTGCTCC |
| 11 | PE8 | GGCCGCCATGGATGCG |
| 12 | PE10A | CTTGAAGGATCCGAGTGG |
| 13 | PE12 | CTTGCTGTTATTCTCCATGC |
| 14 | PE16 | CTGGCTGGCAGCCACGCC |
| 15 | PE20 | TGGTTGCTGAAGCCAGGG |
| 16 | PE22 | ATGCCCAAGAACATGCACG |
| 17 | PE24 | GTTGTTAGGTCAACTTGCG |
| 18 | PE25 | CTCTGTTAGGGCTTCCTCC |
| 19 | PE26 | GAATCAGATTTCGCGAGG |

Primer sequence are set forth 5' to 3'.

EXAMPLE 2
Creation of Ethylene Insensitive Plants Using Arabidopsis Thaliana COL-O Ethylene Insensitive2 Complementary Dna An EIN2 complementary DNA clone called pcEIN2 containing the full length coding region plus 580 base pairs of the 5' end and 300 base pairs of the 3' end of untranslated region was subcloned in the plant transformation vector pKYLX7 to generate a plasmid called pKYLX7:cEIN2. The pKYLX7 vector contains the 35S promoter of the cauliflower mosaic virus and the rbcS-E9 polyadenylation site allowing for the expression of genes in plants (Schardl, C. L., et al., 1987 "Design and construction of a versatile system for the expression of foreign genes in plants" *Gene*, 61:1–11). The pKYLX7:cEIN2 plasmid was introduced into *Agrobacterium tumefaciens* cells (strain C58C1) by electroporation, and the bacterial transformants were selected on LB plates containing kanamycin. Agrobacterium cells carrying the pKYLX7:cEIN2 plasmid or the pKYLX7 plasmid alone were used to infect *Arabidopsis thaliana* ecotype Columbia plants using the vacuum infiltration procedure (Bechtold et al., 1993 "In planta Agrobacterium-mediated transfer by infiltration of adult *Arabidopsis thaliana* plants" *Comptes rendus de Academic des Sciences* 316, 1194–1199). After further growth of the infiltrated plants, seeds (T1 generation) were collected and plated on MS medium supplemented with 1% sucrose and 50 μ/ml kanamycin. Plant lines resistant to kanamycin were selected and transferred to soil for further growth. Seeds (T2 generation) were harvested from the individual T1 plants.

Figure 2B:
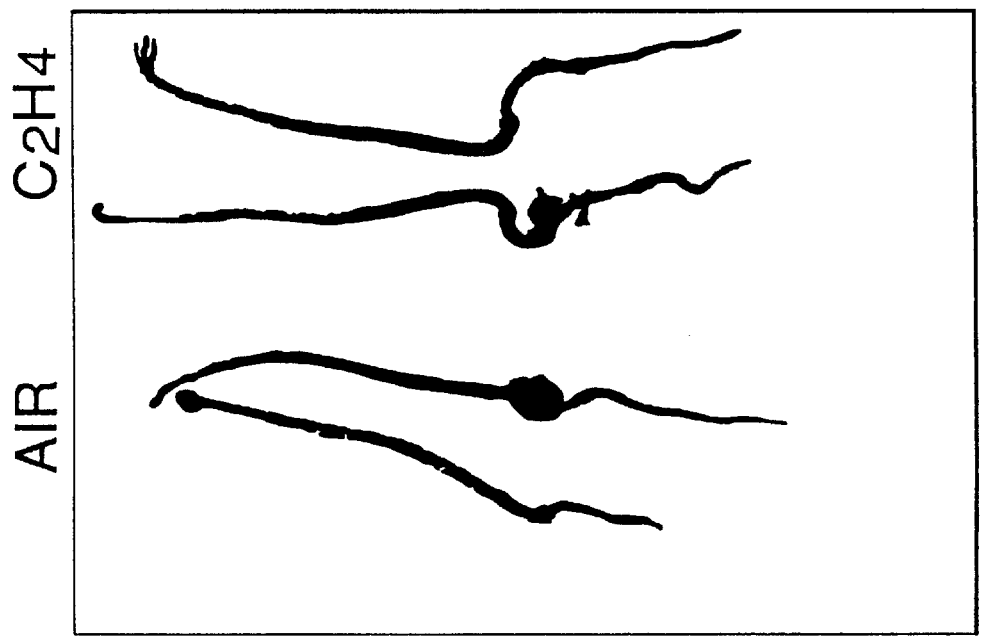
FIGS. 2A and 2B displays Arabidopsis thaliana plants grown in air or ethylene.
Figure 2A:
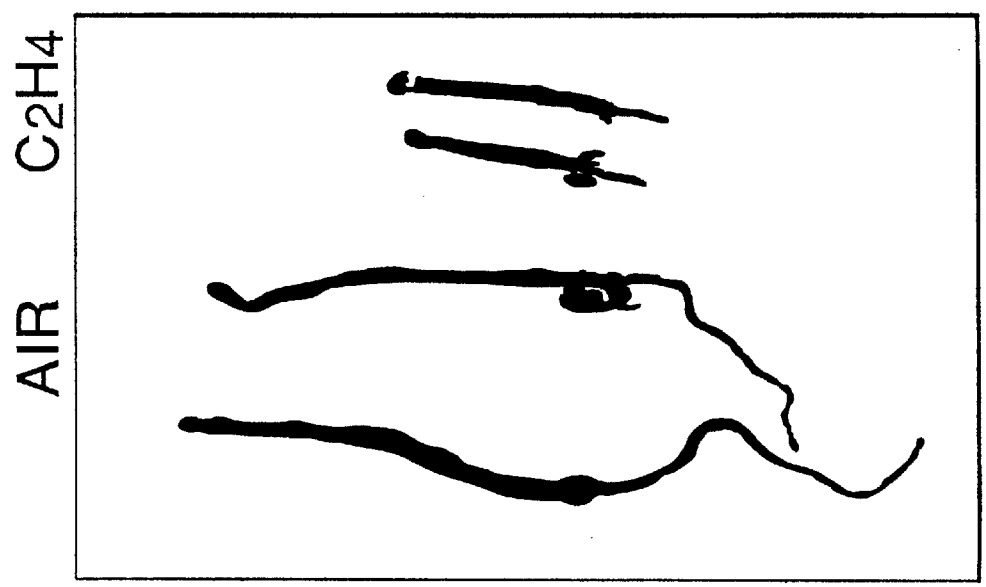

In order to study the effect of the pKYLX7:cEIN2 on the ethylene responses in these plants, transformed plants at the seedling stage were examined for the presence of the ethylene-mediated triple response phenotype (Guzman and Ecker, 1990 "Exploiting the triple response of Arabidopsis to identify ethylene-related mutants", *Plant Cell* 2, 513–523). T2 generation seedlings were plated on MS medium supplemented with 1% sucrose and were germinated and grown in the dark for 3 days in the presence or absence of 10 μl of ethylene/liter of air. Seeds corresponding to 207 T1 independent transformed lines were examined. In six of the transgenic pKYLX7:cEIN2-containing plants, plants were found that showed a strong ethylene insensitive (Ein−) phenotype (FIGS. 2A and 2B). This effect was heritable in subsequent generations and the ethylene insensitivity has not been observed in a similar number of plant lines transformed with the pKYLX plasmid alone. Therefore, the Arabidopsis cEIN2 cDNA can be used to create a plant that is resistant to the effects of ethylene. This approach to the creation of ethylene insensitive plants can be applied to any plant that contains a gene homologous to EIN2.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

What is claimed is:

1. An isolated protein sequence consisting of the amino acid sequence set forth in SEQ ID. NO 3.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 6172 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
TAATAAAGGT GGGGTGAAGA AACCAAATGT TTAACCTGGA AAATTTATTT TAAAAGACGT      60

TTTTTTAGCT ATAAGAAAAA AAAGGATAAT ACCCTTATTT TTACATGTTA TTTACCAGTA     120

ATAATTTTTT TTTTCTCTCT CTCTCTTTGA AGGTGGCACG AGCACCCATA ACCTTCAGAC     180

CTATAGATAC AAATATGTAT GTATACGTTT TTTATATATA AATATTTTAT ATAATTGATT     240

TTTCGATCTT CTTTTATCTC TCTCTTTCGA TGGAACTGAG CTCTTTCTCT CTTTCCTCTT     300

CTTTTCTCTC TCTATCTCTA TCTCTCGTAG CTTGATAAGA GTTTCTCTCT TTTGAAGATC     360

CGTTTCTCTC TCTCTCACTG AGACTATTGT TGTTAGGTCA ACTTGCGATC ATGGCGATTT     420

CGAAGGTGAC TTCTTTCAAA AACCCTAATC CTCTGTTTTT TTTTTTATTT TGCTGGGGGG     480

CTTTGTACGG ACTTTCATGG GTTTTTGTAG CTTTTCCCTC GGCTTTTGCG CAAATGAGAC     540

TTTCTGGGTT TTTTTTCCAG CTTTTTATAA TTTCATCAGG TGGATCGAAT TCGTAGTTTC     600

AGCTTAGATC TCTCTCCCTC TTCATTATCT GGACTTTCCA GACTTGGAGT TCTTCGGGAT     660

TGTTTTCGGT TTCTGGGTTT TGTTTTAATT GCGAGATTTA AGCTTTTTTC TTTTTTACTA     720

CTGTACTTGG TTTGTGGTTG ACCTTTTTTT TCCTTGAAGA TCTGAATGCG TAGATCATAC     780

GGGATCTTTG CATTTTTGTT GCTTTTCGTC AGCGTTACGA TTCTTTTAGC TTCAGTTTAG     840

TTGAAATTTG TATTTTTTTT GAGCTTATCT TCTTTTTGTT GCTGCTTCAT ACTAAGATCA     900

ATTATTGATT TGTAATACTA CTGTATCTGA AGATTTTCAC CATAAAAAAA AAATTCAGGT     960

CTGAAGCTGA TTTCGAATGG TTTGGAGATA TCCGTAGTGG TTAAGCATAT GGAAGTCTAT    1020

GTTCTGCTCT TGGTTGCTCT GTTAGGGCTT CCTCCATTTG GACCAACTTA GCTGAATGTT    1080

GTATGATCTC TCTCCTTGAA GCAGCAAATA AGAAGAAGGT CTGGTCCTTA ACTTAACATC    1140

TGGTTACTAG AGGAAACTTC AGCTATTATT AGGTAAAGAA AGACTGTACA GAGTTGTATA    1200

ACAAGTAAGC GTTAGAGTGG CTTTGTTTGC CTCGGTGATA GAAGAACCGA CTGATTCGTT    1260

GTTGTGTGTT AGCTTTGGAG GGAATCAGAT TTCGCGAGGG AAGGTGTTTT AGATCAAATC    1320
```

```
                                        -continued

TGTGAATTTT ACTCAACTGA GGCTTTTAGT GAACCACGAC TGTAGAGTTG ACCTTGAATC    1380

CTACTCTGAG TAATTATATT ATCAGATAGA TTTAGGATGG AAGCTGAAAT TGTGAATGTG    1440

AGACCTCAGC TAGGGTTTAT CCAGAGAATG GTTCCTGCTC TACTTCCTGT CCTTTTGGTT    1500

TCTGTCGGAT ATATTGATCC CGGGAAATGG GTTGCAAATA TCGAAGGAGG TGCTCGTTTC    1560

GGGTATGACT TGGTGGCAAT TACTCTGCTT TTCAATTTTG CCGCCATCTT ATGCCAATAT    1620

GTTGCAGCTC GCATAAGCGT TGTGACTGGT AAACACTTGG CTCAGGTAAA CATTTTCTG    1680

ATCTCTAAAG AACAAACTTT TTAAAATAAC AAACTGGGCT CTGTGGTTGT CTTGTCACTT    1740

TCTCAAAGTG GAATTCTACT AACCACCTTC TCTATTTTTC TAACATTTTA ATGTTCTTTA    1800

CTGGGACAGA TCTGCAATGA AGAATATGAC AAGTGGACGT GCATGTTCTT GGCATTCAG    1860

GCGGAGTTCT CAGCAATTCT GCTCGACCTT ACCATGGTAG TTACTTACAA TCTTTGCTGT    1920

TCTTAATTTT TTTATTATGT GATAAAATTT TGATTCCTCT GACTTGAGCT TCTCTATTAT    1980

AAACAGGTTG TGGGAGTTGC GCATGCACTT AACCTTTGT TTGGGGTGGA GTTATCCACT    2040

GGAGTGTTTT TGGCCGCCAT GGATGCGTTT TTATTTCCTG TTTTCGCCTC TTTCCTTGTA    2100

TGACTGGTCT TCCTGTCTTG TTTTTTTTCT CCACGTTCTT GAAATAGCAT TATTGGAAAT    2160

TAGCTGACAT GCATACAATT TCTGACAGGA AAATGGTATG GCAAATACAG TATCCATTTA    2220

CTCTGCAGGC CTGGTATTAC TTCTCTATGT ATCTGGCGTC TTGCTGAGTC AGTCTGAGAT    2280

CCCACTCTCT ATGAATGGAG TGTTAACTCG GTTAAATGGA GAGAGCGCAT TCGCACTGAT    2340

GGGTCTTCTT GGCGCAAGCA TCGTCCCTCA CAATTTTTAT ATCCATTCTT ATTTTGCTGG    2400

GGTACCTTTT TTCTCTTTAT ATGTATCTCT CTTTTCTGTT AAGAAGCAAT AATTATACTA    2460

AGCAGTGAAC GCTCTATTAC AGGAAAGTAC ATCTTCGTCT GATGTCGACA AGAGCAGCTT    2520

GTGTCAAGAC CATTTGTTCG CCATCTTTGG TGTCTTCAGC GGACTGTCAC TTGTAAATTA    2580

TGTATTGATG AATGCAGCAG CTAATGTGTT TCACAGTACT GGCCTTGTGG TACTGACTTT    2640

TCACGATGCC TTGTCACTAA TGGAGCAGGT TTGTTCTGAC GGTTTTATGT TCGTATTAGT    2700

CTATAATTCA TTTTTAGGGA AAATGTTCAG AAATCTCTCG TGATTATTAA TTATCTTGTT    2760

CTTGATTGTT GATCACAGGT ATTTATGAGT CCGCTCATTC CAGTGGTCTT TTTGATGCTC    2820

TTGTTCTTCT CTAGTCAAAT TACCGCACTA GCTTGGGCTT TCGGTGGAGA GGTCGTCCTG    2880

CATGACTTCC TGAAGATAGA AATACCCGCT TGGCTTCATC GTGCTACAAT CAGAATTCTT    2940

GCAGTTGCTC CTGCGCTTTA TTGTGTATGG ACATCTGGTG CAGACGGAAT ATACCAGTTA    3000

CTTATATTCA CCCAGGTCTT GGTGGCAATG ATGCTTCCTT GCTCGGTAAT ACCGCTTTTC    3060

CGCATTGCTT CGTCGAGACA AATCATGGGT GTCCATAAAA TCCCTCAGGT TGGCGAGTTC    3120

CTCGCACTTA CAACGTTTTT GGGATTTCTG GGGTTGAATG TTGTTTTTGT TGTTGAGATG    3180

GTATTTGGGA GCAGTGACTG GGCTGGTGGT TTGAGATGGA ATACCGTGAT GGGCACCTCG    3240

ATTCAGTACA CCACTCTGCT TGTATCGTCA TGTGCATCCT TATGCCTGAT ACTCTGGCTG    3300

GCAGCCACGC CGCTGAAATC TGCGAGTAAC AGAGCGGAAG CTCAAATATG GAACATGGAT    3360

GCTCAAAATG CTTTATCTTA TCCATCTGTT CAAGAAGAGG AAATTGAAAG AACAGAAACA    3420

AGGAGGAACG AAGACGAATC AATAGTGCGG TTGGAAAGCA GGGTAAAGGA TCAGTTGGAT    3480

ACTACGTCTG TTACTAGCTC GGTCTATGAT TTGCCAGAGA ACATTCTAAT GACGGATCAA    3540

GAAATCCGTT CGAGCCCTCC AGAGGAAAGA GAGTTGGATG TAAAGTACTC TACCTCTCAA    3600

GTTAGTAGTC TTAAGGAAGA CTCTGATGTA AAGGAACAGT CTGTATTGCA GTCAACAGTG    3660

GTTAATGAGG TCAGTGATAA GGATCTGATT GTTGAAACAA AGATGGCGAA AATTGAACCA    3720
```

-continued

```
ATGAGTCCTG TGGAGAAGAT TGTTAGCATG GAGAATAACA GCAAGTTTAT TGAAAAGGAT      3780
GTTGAAGGGG TTTCATGGGA AACAGAAGAA GCTACCAAAG CTGCTCCTAC AAGCAACTTT      3840
ACTGTCGGAT CTGATGGTCC TCCTTCATTC CGCAGCTTAA GTGGGAAGG GGGAAGTGGG       3900
ACTGGAAGCC TTTCACGGTT GCAAGGTTTG GGACGTGCTG CCCGGAGACA CTTATCTGCG      3960
ATCCTTGATG AATTTTGGGG ACATTTATAT GATTTTCATG GGCAATTGGT TGCTGAAGCC      4020
AGGGCAAAGA AACTAGATCA GCTGTTTGGC ACTGATCAAA AGTCAGCCTC TTCTATGAAA      4080
GCAGATTCGT TTGAAAAGA CATTAGCAGT GGATATTGCA TGTCACCAAC TGCGAAGGGA       4140
ATGGATTCAC AGATGACTTC AAGTTTATAT GATTCACTGA AGCAGCAGAG GACACCGGGA      4200
AGTATCGATT CGTTGTATGG ATTACAAAGA GGTTCGTCAC CGTCACCGTT GGTCAACCGT      4260
ATGCAGATGT TGGGTGCATA TGGTAACACC ACTAATAATA ATAATGCTTA CGAATTGAGT      4320
GAGAGAAGAT ACTCTAGCCT GCGTGCTCCA TCATCTTCAG AGGGTTGGGA ACACCAACAA      4380
CCAGCTACAG TTCACGGATA CCAGATGAAG TCATATGTAG ACAATTTGGC AAAAGAAAGG      4440
CTTGAAGCCT ACAATCCCG TGGAGAGATC CCGACATCGA GATCTATGGC GCTTGGTACA       4500
TTGAGCTATA CACAGCAACT TGCTTTAGCC TTGAAACAGA AGTCCCAGAA TGGTCTAACC      4560
CCTGGACCAG CTCCTGGGTT TGAGAATTTT GCTGGGTCTA AAGCATATC GCGACAATCT       4620
GAAAGATCTT ATTACGGTGT TCCATCTTCT GGCAATACTG ATACTGTTGG CGCAGCAGTA      4680
GCCAATGAGA AAAATATAG TAGCATGCCA GATATCTCAG GATTGTCTAT GTCCGCAAGG       4740
AACATGCATT TACCAAACAA CAAGAGTGGA TACTGGGATC CGTCAAGTGG AGGAGGAGGG     4800
TATGGTGCGT CTTATGGTCG GTAAGCAAT GAATCATCGT TATATTCTAA TTTGGGGTCA       4860
CGGGTGGGAG TACCCTCGAC TTATGATGAC ATTTCTCAAT CAAGAGGAGG CTACAGAGAT      4920
GCCTACAGTT TGCCACAGAG TGCAACAACA GGGACCGGAT CGCTTTGGTC CAGACAGCCC      4980
TTTGAGCAGT TTGGTGTAGC GGAGAGGAAT GGTGCTGTTG GTGAGGAGCT CAGGAATAGA     5040
TCGAATCCGA TCAATATAGA CAACAACGCT TCTTCTAATG TTGATGCAGA GGCTAAGCTT     5100
CTTCAGTCGT TCAGGCACTG TATTCTAAAG CTTATTAAAC TTGAAGGATC CGAGTGGTTG     5160
TTTGGACAAA GCGATGGAGT TGATGAAGAA CTGATTGACC GGGTAGCTGC ACGAGAGAAG    5220
TTTATCTATG AAGCTGAAGC TCGAGAAATA AACCAGGTGG GTCACATGGG GGAGCCACTA    5280
ATTTCATCGG TTCCTAACTG TGGAGATGGT TGCGTTTGGA GAGCTGATTT GATTGTGAGC    5340
TTTGGAGTTT GGTGCATTCA CCGTGTCCTT GACTTGTCTC TCATGGAGAG TCGGCCTGAG    5400
CTTTGGGGAA AGTACACTTA CGTTCTCAAC CGCCTACAGG TAACAAAAAC CGCAGTAGTT    5460
CATTGAAAAT CACAGTTTTG CAGTTTGAAA ATATTGACAT GTATGGATTT AAACAGGGAG   5520
TGATTGATCC GGCGTTCTCA AAGCTGCGGA CACCAATGAC ACCGTGCTTT TGCCTTCAGA    5580
TTCCAGCGAG CCACCAGAGA GCGAGTCCGA CTTCAGCTAA CGGAATGTTA CCTCCGGCTG    5640
CAAAACCGGC TAAAGGCAAA TGCACAACCG CAGTCACACT TCTTGATCTA ATCAAAGACG    5700
TTGAAATGGC AATCTCTTGT AGAAAAGCC GAACCGGTAC AGCTGCAGGT GATGTGGCTT      5760
TCCCAAAGGG GAAAGAGAAT TTGGCTTCGG TTTTGAAGCG GTATAAACGT CGGTTATCGA    5820
ATAAACCAGT AGGTATGAAT CAGGATGGAC CCGGTTCAAG AAAAAACGTG ACTGCGTACG    5880
GATCATTGGG TTGAAGAAGA GAACATTGT GAGAAATCTC ATGATCAAAG TGACGTCGAG     5940
AGGGAAGCCG AAGAATCAAA ACTCTCGCTT TTGATTGCTC CTCTGCTTCG TTAATTGTGT    6000
ATTAAGAAAA GAAGAAAAAA AATGGATTTT TGTTGCTTCA GAATTTTTCG CTCTTTTTTT    6060
```

-continued

```
CTTAATTTGG TTGTAATGTT ATGTTTATAT ACATATATCA TCATCATAGG ACCATAGCTA      6120

CAAACCGAAT CCGGTTTGTG TAATTCTATG CGGAATCATA AAGAAATCGT CG              6172
```

(2) INFORMATION FOR SEQ ID NO:2:

(i) SEQUENCE CHARACTERISTICS:
        (A) LENGTH: 4746 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (ix) FEATURE:
        (A) NAME/KEY: CDS
        (B) LOCATION: 584..4468

(xi) SEQUENCE DESCRIPTION: SEQ ID NO:2:

```
CTTTTCTCTC TCTATCTCTA TCTCTCGTAG CTTGATAAGA GTTTCTCTCT TTTGAAGATC       60

CGTTTCTCTC TCTCTCACTG AGACTATTGT TGTTAGGTCA ACTTGCGATC ATGGCGATTT      120

CGAAGGTCTG AAGCTGATTT CGAATGGTTT GGAGATATCC GTAGTGGTTA AGCATATGGA      180

AGTCTATGTT CTGCTCTTGG TTGCTCTGTT AGGGCTTCCT CCATTTGGAC CAACTTAGCT      240

GAATGTTGTA TGATCTCTCT CCTTGAAGCA GCAAATAAGA AGAAGGTCTG GTCCTTAACT      300

TAACATCTGG TTACTAGAGG AAACTTCAGC TATTATTAGG TAAAGAAAGA CTGTACAGAG      360

TTGTATAACA AGTAAGCGTT AGAGTGGCTT TGTTTGCCTC GGTGATAGAA GAACCGACTG      420

ATTCGTTGTT GTGTGTTAGC TTTGGAGGGA ATCAGATTTC GCGAGGGAAG GTGTTTTAGA      480

TCAAATCTGT GAATTTTACT CAACTGAGGC TTTTAGTGAA CCACGACTGT AGAGTTGACC      540

TTGAATCCTA CTCTGAGTAA TTATATTATC AGATAGATTT AGG ATG GAA GCT GAA        595
                                              Met Glu Ala Glu
                                                1

ATT GTG AAT GTG AGA CCT CAG CTA GGG TTT ATC CAG AGA ATG GTT CCT        643
Ile Val Asn Val Arg Pro Gln Leu Gly Phe Ile Gln Arg Met Val Pro
  5                  10                  15                  20

GCT CTA CTT CCT GTC CTT TTG GTT TCT GTC GGA TAT ATT GAT CCC GGG        691
Ala Leu Leu Pro Val Leu Leu Val Ser Val Gly Tyr Ile Asp Pro Gly
                 25                  30                  35

AAA TGG GTT GCA AAT ATC GAA GGA GGT GCT CGT TTC GGG TAT GAC TTG        739
Lys Trp Val Ala Asn Ile Glu Gly Gly Ala Arg Phe Gly Tyr Asp Leu
             40                  45                  50

GTG GCA ATT ACT CTG CTT TTC AAT TTT GCC GCC ATC TTA TGC CAA TAT        787
Val Ala Ile Thr Leu Leu Phe Asn Phe Ala Ala Ile Leu Cys Gln Tyr
         55                  60                  65

GTT GCA GCT CGC ATA AGC GTT GTG ACT GGT AAA CAC TTG GCT CAG ATC        835
Val Ala Ala Arg Ile Ser Val Val Thr Gly Lys His Leu Ala Gln Ile
     70                  75                  80

TGC AAT GAA GAA TAT GAC AAG TGG ACG TGC ATG TTC TTG GGC ATT CAG        883
Cys Asn Glu Glu Tyr Asp Lys Trp Thr Cys Met Phe Leu Gly Ile Gln
 85                  90                  95                 100

GCG GAG TTC TCA GCA ATT CTG CTC GAC CTT ACC ATG GTT GTG GGA GTT        931
Ala Glu Phe Ser Ala Ile Leu Leu Asp Leu Thr Met Val Val Gly Val
                105                 110                 115

GCG CAT GCA CTT AAC CTT TTG TTT GGG GTG GAG TTA TCC ACT GGA GTG        979
Ala His Ala Leu Asn Leu Leu Phe Gly Val Glu Leu Ser Thr Gly Val
            120                 125                 130
```

```
TTT TTG GCC GCC ATG GAT GCG TTT TTA TTT CCT GTT TTC GCC TCT TTC        1027
Phe Leu Ala Ala Met Asp Ala Phe Leu Phe Pro Val Phe Ala Ser Phe
        135                 140                 145

CTT GAA AAT GGT ATG GCA AAT ACA GTA TCC ATT TAC TCT GCA GGC CTG        1075
Leu Glu Asn Gly Met Ala Asn Thr Val Ser Ile Tyr Ser Ala Gly Leu
    150                 155                 160

GTA TTA CTT CTC TAT GTA TCT GGC GTC TTG CTG AGT CAG TCT GAG ATC        1123
Val Leu Leu Leu Tyr Val Ser Gly Val Leu Leu Ser Gln Ser Glu Ile
165                 170                 175                 180

CCA CTC TCT ATG AAT GGA GTG TTA ACT CGG TTA AAT GGA GAG AGC GCA        1171
Pro Leu Ser Met Asn Gly Val Leu Thr Arg Leu Asn Gly Glu Ser Ala
            185                 190                 195

TTC GCA CTG ATG GGT CTT CTT GGC GCA AGC ATC GTC CCT CAC AAT TTT        1219
Phe Ala Leu Met Gly Leu Leu Gly Ala Ser Ile Val Pro His Asn Phe
        200                 205                 210

TAT ATC CAT TCT TAT TTT GCT GGG GAA AGT ACA TCT TCG TCT GAT GTC        1267
Tyr Ile His Ser Tyr Phe Ala Gly Glu Ser Thr Ser Ser Ser Asp Val
            215                 220                 225

GAC AAG AGC AGC TTG TGT CAA GAC CAT TTG TTC GCC ATC TTT GGT GTC        1315
Asp Lys Ser Ser Leu Cys Gln Asp His Leu Phe Ala Ile Phe Gly Val
230                 235                 240

TTC AGC GGA CTG TCA CTT GTA AAT TAT GTA TTG ATG AAT GCA GCA GCT        1363
Phe Ser Gly Leu Ser Leu Val Asn Tyr Val Leu Met Asn Ala Ala Ala
245                 250                 255                 260

AAT GTG TTT CAC AGT ACT GGC CTT GTG GTA CTG ACT TTT CAC GAT GCC        1411
Asn Val Phe His Ser Thr Gly Leu Val Val Leu Thr Phe His Asp Ala
            265                 270                 275

TTG TCA CTA ATG GAG CAG GTA TTT ATG AGT CCG CTC ATT CCA GTG GTC        1459
Leu Ser Leu Met Glu Gln Val Phe Met Ser Pro Leu Ile Pro Val Val
            280                 285                 290

TTT TTG ATG CTC TTG TTC TTC TCT AGT CAA ATT ACC GCA CTA GCT TGG        1507
Phe Leu Met Leu Leu Phe Phe Ser Ser Gln Ile Thr Ala Leu Ala Trp
            295                 300                 305

GCT TTC GGT GGA GAG GTC GTC CTG CAT GAC TTC CTG AAG ATA GAA ATA        1555
Ala Phe Gly Gly Glu Val Val Leu His Asp Phe Leu Lys Ile Glu Ile
310                 315                 320

CCC GCT TGG CTT CAT CGT GCT ACA ATC AGA ATT CTT GCA GTT GCT CCT        1603
Pro Ala Trp Leu His Arg Ala Thr Ile Arg Ile Leu Ala Val Ala Pro
325                 330                 335                 340

GCG CTT TAT TGT GTA TGG ACA TCT GGT GCA GAC GGA ATA TAC CAG TTA        1651
Ala Leu Tyr Cys Val Trp Thr Ser Gly Ala Asp Gly Ile Tyr Gln Leu
            345                 350                 355

CTT ATA TTC ACC CAG GTC TTG GTG GCA ATG ATG CTT CCT TGC TCG GTA        1699
Leu Ile Phe Thr Gln Val Leu Val Ala Met Met Leu Pro Cys Ser Val
            360                 365                 370

ATA CCG CTT TTC CGC ATT GCT TCG TCG AGA CAA ATC ATG GGT GTC CAT        1747
Ile Pro Leu Phe Arg Ile Ala Ser Ser Arg Gln Ile Met Gly Val His
            375                 380                 385

AAA ATC CCT CAG GTT GGC GAG TTC CTC GCA CTT ACA ACG TTT TTG GGA        1795
Lys Ile Pro Gln Val Gly Glu Phe Leu Ala Leu Thr Thr Phe Leu Gly
    390                 395                 400

TTT CTG GGG TTG AAT GTT GTT TTT GTT GTT GAG ATG GTA TTT GGG AGC        1843
Phe Leu Gly Leu Asn Val Val Phe Val Val Glu Met Val Phe Gly Ser
405                 410                 415                 420

AGT GAC TGG GCT GGT GGT TTG AGA TGG AAT ACC GTG ATG GGC ACC TCG        1891
Ser Asp Trp Ala Gly Gly Leu Arg Trp Asn Thr Val Met Gly Thr Ser
            425                 430                 435

ATT CAG TAC ACC ACT CTG CTT GTA TCG TCA TGT GCA TCC TTA TGC CTG        1939
Ile Gln Tyr Thr Thr Leu Leu Val Ser Ser Cys Ala Ser Leu Cys Leu
            440                 445                 450
```

```
ATA CTC TGG CTG GCA GCC ACG CCG CTG AAA TCT GCG AGT AAC AGA GCG    1987
Ile Leu Trp Leu Ala Ala Thr Pro Leu Lys Ser Ala Ser Asn Arg Ala
            455                 460                 465

GAA GCT CAA ATA TGG AAC ATG GAT GCT CAA AAT GCT TTA TCT TAT CCA    2035
Glu Ala Gln Ile Trp Asn Met Asp Ala Gln Asn Ala Leu Ser Tyr Pro
        470                 475                 480

TCT GTT CAA GAA GAG GAA ATT GAA AGA ACA GAA ACA AGG AGG AAC GAA    2083
Ser Val Gln Glu Glu Glu Ile Glu Arg Thr Glu Thr Arg Arg Asn Glu
485                 490                 495                 500

GAC GAA TCA ATA GTG CGG TTG GAA AGC AGG GTA AAG GAT CAG TTG GAT    2131
Asp Glu Ser Ile Val Arg Leu Glu Ser Arg Val Lys Asp Gln Leu Asp
            505                 510                 515

ACT ACG TCT GTT ACT AGC TCG GTC TAT GAT TTG CCA GAG AAC ATT CTA    2179
Thr Thr Ser Val Thr Ser Ser Val Tyr Asp Leu Pro Glu Asn Ile Leu
                520                 525                 530

ATG ACG GAT CAA GAA ATC CGT TCG AGC CCT CCA GAG GAA AGA GAG TTG    2227
Met Thr Asp Gln Glu Ile Arg Ser Ser Pro Pro Glu Glu Arg Glu Leu
            535                 540                 545

GAT GTA AAG TAC TCT ACC TCT CAA GTT AGT AGT CTT AAG GAA GAC TCT    2275
Asp Val Lys Tyr Ser Thr Ser Gln Val Ser Ser Leu Lys Glu Asp Ser
        550                 555                 560

GAT GTA AAG GAA CAG TCT GTA TTG CAG TCA ACA GTG GTT AAT GAG GTC    2323
Asp Val Lys Glu Gln Ser Val Leu Gln Ser Thr Val Val Asn Glu Val
565                 570                 575                 580

AGT GAT AAG GAT CTG ATT GTT GAA ACA AAG ATG GCG AAA ATT GAA CCA    2371
Ser Asp Lys Asp Leu Ile Val Glu Thr Lys Met Ala Lys Ile Glu Pro
            585                 590                 595

ATG AGT CCT GTG GAG AAG ATT GTT AGC ATG GAG AAT AAC AGC AAG TTT    2419
Met Ser Pro Val Glu Lys Ile Val Ser Met Glu Asn Asn Ser Lys Phe
            600                 605                 610

ATT GAA AAG GAT GTT GAA GGG GTT TCA TGG GAA ACA GAA GAA GCT ACC    2467
Ile Glu Lys Asp Val Glu Gly Val Ser Trp Glu Thr Glu Glu Ala Thr
            615                 620                 625

AAA GCT GCT CCT ACA AGC AAC TTT ACT GTC GGA TCT GAT GGT CCT CCT    2515
Lys Ala Ala Pro Thr Ser Asn Phe Thr Val Gly Ser Asp Gly Pro Pro
            630                 635                 640

TCA TTC CGC AGC TTA AGT GGG GAA GGG GGA AGT GGG ACT GGA AGC CTT    2563
Ser Phe Arg Ser Leu Ser Gly Glu Gly Gly Ser Gly Thr Gly Ser Leu
645                 650                 655                 660

TCA CGG TTG CAA GGT TTG GGA CGT GCT GCC CGG AGA CAC TTA TCT GCG    2611
Ser Arg Leu Gln Gly Leu Gly Arg Ala Ala Arg Arg His Leu Ser Ala
            665                 670                 675

ATC CTT GAT GAA TTT TGG GGA CAT TTA TAT GAT TTT CAT GGG CAA TTG    2659
Ile Leu Asp Glu Phe Trp Gly His Leu Tyr Asp Phe His Gly Gln Leu
            680                 685                 690

GTT GCT GAA GCC AGG GCA AAG AAA CTA GAT CAG CTG TTT GGC ACT GAT    2707
Val Ala Glu Ala Arg Ala Lys Lys Leu Asp Gln Leu Phe Gly Thr Asp
            695                 700                 705

CAA AAG TCA GCC TCT TCT ATG AAA GCA GAT TCG TTT GGA AAA GAC ATT    2755
Gln Lys Ser Ala Ser Ser Met Lys Ala Asp Ser Phe Gly Lys Asp Ile
            710                 715                 720

AGC AGT GGA TAT TGC ATG TCA CCA ACT GCG AAG GGA ATG GAT TCA CAG    2803
Ser Ser Gly Tyr Cys Met Ser Pro Thr Ala Lys Gly Met Asp Ser Gln
725                 730                 735                 740

ATG ACT TCA AGT TTA TAT GAT TCA CTG AAG CAG CAG AGG ACA CCG GGA    2851
Met Thr Ser Ser Leu Tyr Asp Ser Leu Lys Gln Gln Arg Thr Pro Gly
            745                 750                 755

AGT ATC GAT TCG TTG TAT GGA TTA CAA AGA GGT TCG TCA CCG TCA CCG    2899
Ser Ile Asp Ser Leu Tyr Gly Leu Gln Arg Gly Ser Ser Pro Ser Pro
```

```
                760                   765                   770
TTG GTC AAC CGT ATG CAG ATG TTG GGT GCA TAT GGT AAC ACC ACT AAT    2947
Leu Val Asn Arg Met Gln Met Leu Gly Ala Tyr Gly Asn Thr Thr Asn
        775                   780                   785

AAT AAT AAT GCT TAC GAA TTG AGT GAG AGA AGA TAC TCT AGC CTG CGT    2995
Asn Asn Asn Ala Tyr Glu Leu Ser Glu Arg Arg Tyr Ser Ser Leu Arg
790                   795                   800

GCT CCA TCA TCT TCA GAG GGT TGG GAA CAC CAA CAA CCA GCT ACA GTT    3043
Ala Pro Ser Ser Ser Glu Gly Trp Glu His Gln Gln Pro Ala Thr Val
805                   810                   815                   820

CAC GGA TAC CAG ATG AAG TCA TAT GTA GAC AAT TTG GCA AAA GAA AGG    3091
His Gly Tyr Gln Met Lys Ser Tyr Val Asp Asn Leu Ala Lys Glu Arg
                825                   830                   835

CTT GAA GCC TTA CAA TCC CGT GGA GAG ATC CCG ACA TCG AGA TCT ATG    3139
Leu Glu Ala Leu Gln Ser Arg Gly Glu Ile Pro Thr Ser Arg Ser Met
            840                   845                   850

GCG CTT GGT ACA TTG AGC TAT ACA CAG CAA CTT GCT TTA GCC TTG AAA    3187
Ala Leu Gly Thr Leu Ser Tyr Thr Gln Gln Leu Ala Leu Ala Leu Lys
        855                   860                   865

CAG AAG TCC CAG AAT GGT CTA ACC CCT GGA CCA GCT CCT GGG TTT GAG    3235
Gln Lys Ser Gln Asn Gly Leu Thr Pro Gly Pro Ala Pro Gly Phe Glu
    870                   875                   880

AAT TTT GCT GGG TCT AGA AGC ATA TCG CGA CAA TCT GAA AGA TCT TAT    3283
Asn Phe Ala Gly Ser Arg Ser Ile Ser Arg Gln Ser Glu Arg Ser Tyr
885                   890                   895                   900

TAC GGT GTT CCA TCT TCT GGC AAT ACT GAT ACT GTT GGC GCA GCA GTA    3331
Tyr Gly Val Pro Ser Ser Gly Asn Thr Asp Thr Val Gly Ala Ala Val
                905                   910                   915

GCC AAT GAG AAA AAA TAT AGT AGC ATG CCA GAT ATC TCA GGA TTG TCT    3379
Ala Asn Glu Lys Lys Tyr Ser Ser Met Pro Asp Ile Ser Gly Leu Ser
            920                   925                   930

ATG TCC GCA AGG AAC ATG CAT TTA CCA AAC AAC AAG AGT GGA TAC TGG    3427
Met Ser Ala Arg Asn Met His Leu Pro Asn Asn Lys Ser Gly Tyr Trp
        935                   940                   945

GAT CCG TCA AGT GGA GGA GGA GGG TAT GGT GCG TCT TAT GGT CGG TTA    3475
Asp Pro Ser Ser Gly Gly Gly Gly Tyr Gly Ala Ser Tyr Gly Arg Leu
    950                   955                   960

AGC AAT GAA TCA TCG TTA TAT TCT AAT TTG GGG TCA CGG GTG GGA GTA    3523
Ser Asn Glu Ser Ser Leu Tyr Ser Asn Leu Gly Ser Arg Val Gly Val
965                   970                   975                   980

CCC TCG ACT TAT GAT GAC ATT TCT CAA TCA AGA GGA GGC TAC AGA GAT    3571
Pro Ser Thr Tyr Asp Asp Ile Ser Gln Ser Arg Gly Gly Tyr Arg Asp
                985                   990                   995

GCC TAC AGT TTG CCA CAG AGT GCA ACA ACA GGG ACC GGA TCG CTT TGG    3619
Ala Tyr Ser Leu Pro Gln Ser Ala Thr Thr Gly Thr Gly Ser Leu Trp
            1000                  1005                  1010

TCC AGA CAG CCC TTT GAG CAG TTT GGT GTA GCG GAG AGG AAT GGT GCT    3667
Ser Arg Gln Pro Phe Glu Gln Phe Gly Val Ala Glu Arg Asn Gly Ala
        1015                  1020                  1025

GTT GGT GAG GAG CTC AGG AAT AGA TCG AAT CCG ATC AAT ATA GAC AAC    3715
Val Gly Glu Glu Leu Arg Asn Arg Ser Asn Pro Ile Asn Ile Asp Asn
    1030                  1035                  1040

AAC GCT TCT TCT AAT GTT GAT GCA GAG GCT AAG CTT CTT CAG TCG TTC    3763
Asn Ala Ser Ser Asn Val Asp Ala Glu Ala Lys Leu Leu Gln Ser Phe
1045                  1050                  1055                  1060

AGG CAC TGT ATT CTA AAG CTT ATT AAA CTT GAA GGA TCC GAG TGG TTG    3811
Arg His Cys Ile Leu Lys Leu Ile Lys Leu Glu Gly Ser Glu Trp Leu
                1065                  1070                  1075

TTT GGA CAA AGC GAT GGA GTT GAT GAA GAA CTG ATT GAC CGG GTA GCT    3859
```

```
Phe Gly Gln Ser Asp Gly Val Asp Glu Glu Leu Ile Asp Arg Val Ala
            1080                1085                1090

GCA CGA GAG AAG TTT ATC TAT GAA GCT GAA GCT CGA GAA ATA AAC CAG    3907
Ala Arg Glu Lys Phe Ile Tyr Glu Ala Glu Ala Arg Glu Ile Asn Gln
        1095                1100                1105

GTG GGT CAC ATG GGG GAG CCA CTA ATT TCA TCG GTT CCT AAC TGT GGA    3955
Val Gly His Met Gly Glu Pro Leu Ile Ser Ser Val Pro Asn Cys Gly
    1110                1115                1120

GAT GGT TGC GTT TGG AGA GCT GAT TTG ATT GTG AGC TTT GGA GTT TGG    4003
Asp Gly Cys Val Trp Arg Ala Asp Leu Ile Val Ser Phe Gly Val Trp
1125                1130                1135                1140

TGC ATT CAC CGT GTC CTT GAC TTG TCT CTC ATG GAG AGT CGG CCT GAG    4051
Cys Ile His Arg Val Leu Asp Leu Ser Leu Met Glu Ser Arg Pro Glu
                1145                1150                1155

CTT TGG GGA AAG TAC ACT TAC GTT CTC AAC CGC CTA CAG GGA GTG ATT    4099
Leu Trp Gly Lys Tyr Thr Tyr Val Leu Asn Arg Leu Gln Gly Val Ile
            1160                1165                1170

GAT CCG GCG TTC TCA AAG CTG CGG ACA CCA ATG ACA CCG TGC TTT TGC    4147
Asp Pro Ala Phe Ser Lys Leu Arg Thr Pro Met Thr Pro Cys Phe Cys
        1175                1180                1185

CTT CAG ATT CCA GCG AGC CAC CAG AGA GCG AGT CCG ACT TCA GCT AAC    4195
Leu Gln Ile Pro Ala Ser His Gln Arg Ala Ser Pro Thr Ser Ala Asn
    1190                1195                1200

GGA ATG TTA CCT CCG GCT GCA AAA CCG GCT AAA GGC AAA TGC ACA ACC    4243
Gly Met Leu Pro Pro Ala Ala Lys Pro Ala Lys Gly Lys Cys Thr Thr
1205                1210                1215                1220

GCA GTC ACA CTT CTT GAT CTA ATC AAA GAC GTT GAA ATG GCA ATC TCT    4291
Ala Val Thr Leu Leu Asp Leu Ile Lys Asp Val Glu Met Ala Ile Ser
                1225                1230                1235

TGT AGA AAA GGC CGA ACC GGT ACA GCT GCA GGT GAT GTG GCT TTC CCA    4339
Cys Arg Lys Gly Arg Thr Gly Thr Ala Ala Gly Asp Val Ala Phe Pro
            1240                1245                1250

AAG GGG AAA GAG AAT TTG GCT TCG GTT TTG AAG CGG TAT AAA CGT CGG    4387
Lys Gly Lys Glu Asn Leu Ala Ser Val Leu Lys Arg Tyr Lys Arg Arg
        1255                1260                1265

TTA TCG AAT AAA CCA GTA GGT ATG AAT CAG GAT GGA CCC GGT TCA AGA    4435
Leu Ser Asn Lys Pro Val Gly Met Asn Gln Asp Gly Pro Gly Ser Arg
    1270                1275                1280

AAA AAC GTG ACT GCG TAC GGA TCA TTG GGT TGA AGAAGAAGAA CATTGTGAGA  4488
Lys Asn Val Thr Ala Tyr Gly Ser Leu Gly *
1285                1290                1295

AATCTCATGA TCAAAGTGAC GTCGAGAGGG AAGCCGAAGA ATCAAAACTC TCGCTTTTGA  4548

TTGCTCCTCT GCTTCGTTAA TTGTGTATTA AGAAAAGAAG AAAAAAAATG GATTTTTGTT  4608

GCTTCAGAAT TTTTCGCTCT TTTTTTCTTA ATTTGGTTGT AATGTTATGT TTATATACAT  4668

ATATCATCAT CATAGGACCA TAGCTACAAA CCGAATCCGG TTTGTGTAAT TCTATGCGGA  4728

ATCATAAAGA AATCGTCG                                                4746

(2) INFORMATION FOR SEQ ID NO:3:

(i) SEQUENCE CHARACTERISTICS:
        (A) LENGTH: 1294 amino acids
        (B) TYPE: amino acid
        (D) TOPOLOGY: linear (ii) MOLECULE TYPE: protein (xi) SEQUENCE DESCRIPTION: SEQ ID NO:3:

Met Glu Ala Glu Ile Val Asn Val Arg Pro Gln Leu Gly Phe Ile Gln
  1               5                  10                  15
```

-continued

```
Arg Met Val Pro Ala Leu Leu Pro Val Leu Val Ser Val Gly Tyr
         20                  25                  30

Ile Asp Pro Gly Lys Trp Val Ala Asn Ile Glu Gly Gly Ala Arg Phe
         35                  40                  45

Gly Tyr Asp Leu Val Ala Ile Thr Leu Leu Phe Asn Phe Ala Ala Ile
         50                  55                  60

Leu Cys Gln Tyr Val Ala Ala Arg Ile Ser Val Val Thr Gly Lys His
65                   70                  75                  80

Leu Ala Gln Ile Cys Asn Glu Glu Tyr Asp Lys Trp Thr Cys Met Phe
                 85                  90                  95

Leu Gly Ile Gln Ala Glu Phe Ser Ala Ile Leu Leu Asp Leu Thr Met
                100                 105                 110

Val Val Gly Val Ala His Ala Leu Asn Leu Leu Phe Gly Val Glu Leu
                115                 120                 125

Ser Thr Gly Val Phe Leu Ala Ala Met Asp Ala Phe Leu Phe Pro Val
            130                 135                 140

Phe Ala Ser Phe Leu Glu Asn Gly Met Ala Asn Thr Val Ser Ile Tyr
145                 150                 155                 160

Ser Ala Gly Leu Val Leu Leu Leu Tyr Val Ser Gly Val Leu Leu Ser
                165                 170                 175

Gln Ser Glu Ile Pro Leu Ser Met Asn Gly Val Leu Thr Arg Leu Asn
                180                 185                 190

Gly Glu Ser Ala Phe Ala Leu Met Gly Leu Leu Gly Ala Ser Ile Val
                195                 200                 205

Pro His Asn Phe Tyr Ile His Ser Tyr Phe Ala Gly Glu Ser Thr Ser
            210                 215                 220

Ser Ser Asp Val Asp Lys Ser Ser Leu Cys Gln Asp His Leu Phe Ala
225                 230                 235                 240

Ile Phe Gly Val Phe Ser Gly Leu Ser Leu Val Asn Tyr Val Leu Met
                245                 250                 255

Asn Ala Ala Ala Asn Val Phe His Ser Thr Gly Leu Val Val Leu Thr
            260                 265                 270

Phe His Asp Ala Leu Ser Leu Met Glu Gln Val Phe Met Ser Pro Leu
            275                 280                 285

Ile Pro Val Val Phe Leu Met Leu Leu Phe Phe Ser Ser Gln Ile Thr
            290                 295                 300

Ala Leu Ala Trp Ala Phe Gly Gly Glu Val Val Leu His Asp Phe Leu
305                 310                 315                 320

Lys Ile Glu Ile Pro Ala Trp Leu His Arg Ala Thr Ile Arg Ile Leu
                325                 330                 335

Ala Val Ala Pro Ala Leu Tyr Cys Val Trp Thr Ser Gly Ala Asp Gly
            340                 345                 350

Ile Tyr Gln Leu Leu Ile Phe Thr Gln Val Leu Val Ala Met Met Leu
            355                 360                 365

Pro Cys Ser Val Ile Pro Leu Phe Arg Ile Ala Ser Ser Arg Gln Ile
            370                 375                 380

Met Gly Val His Lys Ile Pro Gln Val Gly Glu Phe Leu Ala Leu Thr
385                 390                 395                 400

Thr Phe Leu Gly Phe Leu Gly Leu Asn Val Val Phe Val Val Glu Met
                405                 410                 415

Val Phe Gly Ser Ser Asp Trp Ala Gly Gly Leu Arg Trp Asn Thr Val
            420                 425                 430
```

-continued

```
Met Gly Thr Ser Ile Gln Tyr Thr Thr Leu Leu Val Ser Ser Cys Ala
            435                 440                 445

Ser Leu Cys Leu Ile Leu Trp Leu Ala Ala Thr Pro Leu Lys Ser Ala
            450                 455                 460

Ser Asn Arg Ala Glu Ala Gln Ile Trp Asn Met Asp Ala Gln Asn Ala
465                 470                 475                 480

Leu Ser Tyr Pro Ser Val Gln Glu Glu Ile Glu Arg Thr Glu Thr
            485                 490                 495

Arg Arg Asn Glu Asp Glu Ser Ile Val Arg Leu Glu Ser Arg Val Lys
                500                 505                 510

Asp Gln Leu Asp Thr Thr Ser Val Thr Ser Ser Val Tyr Asp Leu Pro
            515                 520                 525

Glu Asn Ile Leu Met Thr Asp Gln Glu Ile Arg Ser Ser Pro Pro Glu
            530                 535                 540

Glu Arg Glu Leu Asp Val Lys Tyr Ser Thr Ser Gln Val Ser Ser Leu
545                 550                 555                 560

Lys Glu Asp Ser Asp Val Lys Glu Gln Ser Val Leu Gln Ser Thr Val
                565                 570                 575

Val Asn Glu Val Ser Asp Lys Asp Leu Ile Val Glu Thr Lys Met Ala
            580                 585                 590

Lys Ile Glu Pro Met Ser Pro Val Glu Lys Ile Val Ser Met Glu Asn
            595                 600                 605

Asn Ser Lys Phe Ile Glu Lys Asp Val Glu Gly Val Ser Trp Glu Thr
610                 615                 620

Glu Glu Ala Thr Lys Ala Ala Pro Thr Ser Asn Phe Thr Val Gly Ser
625                 630                 635                 640

Asp Gly Pro Pro Ser Phe Arg Ser Leu Ser Gly Glu Gly Gly Ser Gly
                645                 650                 655

Thr Gly Ser Leu Ser Arg Leu Gln Gly Leu Gly Arg Ala Ala Arg Arg
            660                 665                 670

His Leu Ser Ala Ile Leu Asp Glu Phe Trp Gly His Leu Tyr Asp Phe
            675                 680                 685

His Gly Gln Leu Val Ala Glu Ala Arg Ala Lys Lys Leu Asp Gln Leu
690                 695                 700

Phe Gly Thr Asp Gln Lys Ser Ala Ser Ser Met Lys Ala Asp Ser Phe
705                 710                 715                 720

Gly Lys Asp Ile Ser Ser Gly Tyr Cys Met Ser Pro Thr Ala Lys Gly
                725                 730                 735

Met Asp Ser Gln Met Thr Ser Ser Leu Tyr Asp Ser Leu Lys Gln Gln
            740                 745                 750

Arg Thr Pro Gly Ser Ile Asp Ser Leu Tyr Gly Leu Gln Arg Gly Ser
            755                 760                 765

Ser Pro Ser Pro Leu Val Asn Arg Met Gln Met Leu Gly Ala Tyr Gly
            770                 775                 780

Asn Thr Thr Asn Asn Asn Ala Tyr Glu Leu Ser Glu Arg Arg Tyr
785                 790                 795                 800

Ser Ser Leu Arg Ala Pro Ser Ser Glu Gly Trp Glu His Gln Gln
                805                 810                 815

Pro Ala Thr Val His Gly Tyr Gln Met Lys Ser Tyr Val Asp Asn Leu
            820                 825                 830

Ala Lys Glu Arg Leu Glu Ala Leu Gln Ser Arg Gly Glu Ile Pro Thr
            835                 840                 845

Ser Arg Ser Met Ala Leu Gly Thr Leu Ser Tyr Thr Gln Gln Leu Ala
```

-continued

```
            850                 855                 860
Leu Ala Leu Lys Gln Lys Ser Gln Asn Gly Leu Thr Pro Gly Pro Ala
865                 870                 875                 880
Pro Gly Phe Glu Asn Phe Ala Gly Ser Arg Ser Ile Ser Arg Gln Ser
                    885                 890                 895
Glu Arg Ser Tyr Tyr Gly Val Pro Ser Ser Gly Asn Thr Asp Thr Val
                900                 905                 910
Gly Ala Ala Val Ala Asn Glu Lys Lys Tyr Ser Ser Met Pro Asp Ile
            915                 920                 925
Ser Gly Leu Ser Met Ser Ala Arg Asn Met His Leu Pro Asn Asn Lys
        930                 935                 940
Ser Gly Tyr Trp Asp Pro Ser Gly Gly Gly Tyr Gly Ala Ser
945                 950                 955                 960
Tyr Gly Arg Leu Ser Asn Glu Ser Ser Leu Tyr Ser Asn Leu Gly Ser
                965                 970                 975
Arg Val Gly Val Pro Ser Thr Tyr Asp Asp Ile Ser Gln Ser Arg Gly
                980                 985                 990
Gly Tyr Arg Asp Ala Tyr Ser Leu Pro Gln Ser Ala Thr Thr Gly Thr
            995                 1000                1005
Gly Ser Leu Trp Ser Arg Gln Pro Phe Glu Gln Phe Gly Val Ala Glu
        1010                1015                1020
Arg Asn Gly Ala Val Gly Glu Glu Leu Arg Asn Arg Ser Asn Pro Ile
1025                1030                1035                1040
Asn Ile Asp Asn Asn Ala Ser Ser Asn Val Asp Ala Glu Ala Lys Leu
                1045                1050                1055
Leu Gln Ser Phe Arg His Cys Ile Leu Lys Leu Ile Lys Leu Glu Gly
                1060                1065                1070
Ser Glu Trp Leu Phe Gly Gln Ser Asp Gly Val Asp Glu Glu Leu Ile
            1075                1080                1085
Asp Arg Val Ala Ala Arg Glu Lys Phe Ile Tyr Glu Ala Glu Ala Arg
        1090                1095                1100
Glu Ile Asn Gln Val Gly His Met Gly Glu Pro Leu Ile Ser Ser Val
1105                1110                1115                1120
Pro Asn Cys Gly Asp Gly Cys Val Trp Arg Ala Asp Leu Ile Val Ser
                1125                1130                1135
Phe Gly Val Trp Cys Ile His Arg Val Leu Asp Leu Ser Leu Met Glu
                1140                1145                1150
Ser Arg Pro Glu Leu Trp Gly Lys Tyr Thr Tyr Val Leu Asn Arg Leu
            1155                1160                1165
Gln Gly Val Ile Asp Pro Ala Phe Ser Lys Leu Arg Thr Pro Met Thr
        1170                1175                1180
Pro Cys Phe Cys Leu Gln Ile Pro Ala Ser His Gln Arg Ala Ser Pro
1185                1190                1195                1200
Thr Ser Ala Asn Gly Met Leu Pro Pro Ala Ala Lys Pro Ala Lys Gly
                1205                1210                1215
Lys Cys Thr Thr Ala Val Thr Leu Leu Asp Leu Ile Lys Asp Val Glu
                1220                1225                1230
Met Ala Ile Ser Cys Arg Lys Gly Arg Thr Gly Thr Ala Ala Gly Asp
            1235                1240                1245
Val Ala Phe Pro Lys Gly Lys Glu Asn Leu Ala Ser Val Leu Lys Arg
        1250                1255                1260
Tyr Lys Arg Arg Leu Ser Asn Lys Pro Val Gly Met Asn Gln Asp Gly
1265                1270                1275                1280
```

Pro Gly Ser Arg Lys Asn Val Thr Ala Tyr Gly Ser Leu Gly
        1285                1290                1295

(2) INFORMATION FOR SEQ ID NO: 4:

(i) SEQUENCE CHARACTERISTICS:
        (A) LENGTH: 23 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 4:

GGATCCTCTA GTCAAATTAC CGC                                              23

(2) INFORMATION FOR SEQ ID NO: 5:

(i) SEQUENCE CHARACTERISTICS:
        (A) LENGTH: 24 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 5:

AGATCTGGTA TATTCCGTCT GCAC                                             24

(2) INFORMATION FOR SEQ ID NO: 6:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 6:

CCGGATTCGG TTTGTAGC                                                    18

(2) INFORMATION FOR SEQ ID NO: 7:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 7:

GAAAGCCACA TCACCTGC                                                    18

(2) INFORMATION FOR SEQ ID NO: 8:

(i) SEQUENCE CHARACTERISTICS:
        (A) LENGTH: 17 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 8:

GACACCGGGA AGTATCG                                                     17

(2) INFORMATION FOR SEQ ID NO: 9:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 9:

```
CTGCTTTCAT AGAAGAGGC                                              19
```

(2) INFORMATION FOR SEQ ID NO: 10:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 10:

```
GTCAGAACAA ACCTGCTCC                                              19
```

(2) INFORMATION FOR SEQ ID NO: 11:

(i) SEQUENCE CHARACTERISTICS:
        (A) LENGTH: 16 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:11:

```
GGCCGCCATG GATGCG                                                 16
```

(2) INFORMATION FOR SEQ ID NO: 12:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 12:

```
CTTGAAGGAT CCGAGTGG                                               18
```

(2) INFORMATION FOR SEQ ID NO: 13:

(i) SEQUENCE CHARACTERISTICS:
        (A) LENGTH: 20 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 13:

```
CTTGCTGTTA TTCTCCATGC                                             20
```

(2) INFORMATION FOR SEQ ID NO: 14:

(i) SEQUENCE CHARACTERISTICS (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 14:

CTGGCTGGCA GCCACGCC                                                 18

(2) INFORMATION FOR SEQ ID NO: 15:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 15:

TGGTTGCTGA AGCCAGGG                                                 18

(2) INFORMATION FOR SEQ ID NO: 16:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 16:

ATGCCCAAGA ACATGCACG                                                19

(2) INFORMATION FOR SEQ ID NO: 17:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 17:

GTTGTTAGGT CAACTTGCG                                                19

(2) INFORMATION FOR SEQ ID NO: 18:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO: 18:

CTCTGTTAGG GCTTCCTCC                                                19

(2) INFORMATION FOR SEQ ID NO: 19:

(i) SEQUENCE CHARACTERISTICS:
        (A) LENGTH: 18 nucleic acids
        (B) TYPE: nucleic acid
        (C) STRANDEDNESS: single
        (D) TOPOLOGY: linear -continued (iv) ANTI-SENSE: no (xi) SEQUENCE DESCRIPTION: SEQ ID NO: 19:

GAATCAGATT TCGCGAGG                                                                                        18